(12) United States Patent
Van Der Sluis (10) Patent No.: US 11,333,512 B2
(45) Date of Patent: May 17, 2022

(54) EVIDENCE BASED PERSONALIZED HEALTH ADVICE FOR POLLUTED AIR

(71) Applicant: KONINKLIJKE PHILIPS N.V., Eindhoven (NL)

(72) Inventor: Paul Van Der Sluis, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 367 days.

(21) Appl. No.: 16/609,238

(22) PCT Filed: May 4, 2018

(86) PCT No.: PCT/EP2018/061549
§ 371 (c)(1),
(2) Date: Oct. 29, 2019

(87) PCT Pub. No.: WO2018/202871
PCT Pub. Date: Nov. 8, 2018

(65) Prior Publication Data
US 2020/0182641 A1    Jun. 11, 2020

(30) Foreign Application Priority Data

May 4, 2017 (EP) .................................. 17169430

(51) Int. Cl.
*G01C 21/34* (2006.01)
*G16H 20/30* (2018.01)
(Continued)

(52) U.S. Cl.
CPC ........ *G01C 21/3461* (2013.01); *A61B 5/0205* (2013.01); *A61B 5/1118* (2013.01);
(Continued)

(58) Field of Classification Search
None
See application file for complete search history.

(56) References Cited

U.S. PATENT DOCUMENTS

2012/0293315 A1    11/2012    Schunder
2013/0036080 A1*    2/2013    Kane-Esrig ............ G16H 50/50
                                                                  706/46
(Continued)

FOREIGN PATENT DOCUMENTS

CN    103234883    8/2013
CN    104217126    12/2014
(Continued)

OTHER PUBLICATIONS

International Search Report and Written Opinion dated Jul. 5, 2018 for International Application No. PCT/EP2018/061549 Filed May 4, 2018.
(Continued)

*Primary Examiner* — Kelly D Williams (57) ABSTRACT

The invention provides a method for determining a transportation direction (TD) for a user, the method comprising: receiving a current location (CL) of the user; receiving a pollution based input value (PIV) related to air pollution in a geographical area (GA) including the current location (CL); determining the transportation direction (TD) using the pollution based input value such that the user is subjected to a lowest level of pollution and/or such that a predefined maximum level of pollution to which the user is subjected is not exceeded; and retrieving a human activity based input value, wherein the human activity based input value is based on activity data from a portable device (100) configured to sense an activity level of the human wearing the portable device (100); and updating the transportation direction (TD) using the human activity based input value (HAIV).

14 Claims, 2 Drawing Sheets

(51) Int. Cl.

| | |
|---|---|
| *G16H 40/67* | (2018.01) |
| *G06F 16/29* | (2019.01) |
| *A61B 5/0205* | (2006.01) |
| *A61B 5/11* | (2006.01) |
| *A61B 5/00* | (2006.01) |
| *A61B 7/00* | (2006.01) |
| *G01C 21/36* | (2006.01) |
| *A61B 5/021* | (2006.01) |
| *A61B 5/024* | (2006.01) |
| *G08G 1/01* | (2006.01) |
| *G06Q 50/26* | (2012.01) |

(52) U.S. Cl.
CPC ............ *A61B 5/4266* (2013.01); *A61B 7/003* (2013.01); *G01C 21/3691* (2013.01); *G01C 21/3697* (2013.01); *G06F 16/29* (2019.01); *G08G 1/0129* (2013.01); *G16H 20/30* (2018.01); *G16H 40/67* (2018.01); *A61B 5/021* (2013.01); *A61B 5/024* (2013.01); *G06Q 50/265* (2013.01); *G08G 1/0112* (2013.01)

(56) References Cited

U.S. PATENT DOCUMENTS

| | | |
|---|---|---|
| 2013/0080053 A1 | 3/2013 | Rakshit |
| 2013/0144527 A1* | 6/2013 | Kuhnreichi ............. G06F 17/00 702/2 |
| 2014/0278100 A1 | 9/2014 | Hirabayashi |
| 2014/0303885 A1 | 10/2014 | Kamada |
| 2017/0245808 A1* | 8/2017 | Jain ....................... A61B 5/1118 |

FOREIGN PATENT DOCUMENTS

| | | | |
|---|---|---|---|
| DE | 102015013596 | 4/2016 | |
| FR | 3046345 A1 * | 7/2017 | ........... A61B 5/4866 |
| JP | 2001101561 | 4/2001 | |
| JP | 2006275720 A | 10/2006 | |
| KR | 1020050004967 A | 1/2005 | |
| KR | 201206141 | 6/2012 | |
| RU | 2015134106 A | 2/2017 | |

OTHER PUBLICATIONS

Ribeiro et al: "Route planning for soft modes of transport: healthy routes", Urban Transport XVII, vol. 1, Jun. 6, 2011.

Chang et al: "Estimating Real-Time Traffic Carbon Dioxide Emissions Based on Intelligent Transportation System Technologies", IEEE Transactions on Intelligent Transportation Systems, IEEE, Piscataway, NJ, USA, vol. 14, No. 1, Mar. 1, 2013.

* cited by examiner

EVIDENCE BASED PERSONALIZED HEALTH ADVICE FOR POLLUTED AIR

CROSS REFERENCE TO RELATED APPLICATIONS

This application is the U.S. National Phase application under 35 U.S.C. § 371 of International Application No. PCT/EP2018/061549 filed May 4, 2018, published as WO 2018/202871 on Nov. 8, 2018, which claims the benefit of European Patent Application Number 17169430.0 filed May 4, 2017. These applications are hereby incorporated by reference herein.

FIELD OF THE INVENTION

The invention relates to a method for determining a transportation direction, a data carrier having stored thereon program instructions for such method, as well as a computer implemented system for executing such method.

BACKGROUND OF THE INVENTION

Dynamic route recommendation based on pollution data is known in the art. US2013080053, for instance, describes about recommending a route. An indication of an origin and a destination is received. Data describing a plurality of navigation routes between the origin and the destination is received. A plurality of pollution score values corresponding to each of the plurality of navigation routes is determined. A cumulative score value is determined for each of the plurality of navigation routes. The data describing the plurality of navigation routes between the origin and the destination and the corresponding plurality of pollution score values and cumulative score values is transmitted.

US20140278100A1 discloses a head or face-mounted device that provides guidance information to a user based on environmental information that it acquires.

US20140303885A1 discloses a navigation apparatus that provides in real-time a movement direction of an object based on first and second environmental information.

Publication "route planning for soft modes of transport—healthy routes" by Paulo Ribeiro and Jose F. G. Mendes discloses a healthy route planner taking into account street network maps and the associated pollution.

SUMMARY OF THE INVENTION

Particulate air pollution has been associated with increased morbidity and mortality from respiratory and cardiac disease. Particles less than 100 nm in diameter (ultrafine particles, UFP) are ubiquitous in ambient particulate pollution, dominate particle number and surface area concentrations because of their small size. High numbers of UFP are emitted by internal combustion processes, including both diesel and gasoline powered engines. Also particles between 0.1 and 10 µm (the so-called fine particles, FP) may create a health hazard. These particulates are in general produced by all kinds of wear processes that are ubiquitous in the modern world.

The health effects are aggravated when individuals start to become physically active. This is a very significant effect and is the reason that at times of high air pollution people are advices to refrain from exercise. Not only because people breath in more air and thus more pollutants, but also because the amount of deposited particles increases with exercise. So a larger fraction of more pollutants are deposited inside the human body when physically active. The impact can be a factor 10 or larger and is thus of extreme importance. So for individuals that care about their health it is important to know the concentration of UFP and FP at the location where they are, so they can adapt their behavior accordingly. Especially for people at risk (COPD patients, asthma patients) this is important.

Warning systems may provide information for large areas, like entire states or countries, and thus on a detail level that may be much too low, and in a detail level which also does not allow an individual user to define the best route when a relocation is necessary, even under outdoor conditions that are less desirable.

Hence, it is an aspect of the invention to provide an alternative that defines a transport direction or relocation, which preferably further at least partly obviates one or more of above-described drawbacks. The present invention may have as object to overcome or ameliorate at least one of the disadvantages of the prior art, or to provide a useful alternative.

For instance, in embodiments it may be possible to calculate the FP and UFP concentrations near a person, measure the activity level of that person and give advice accordingly. The advice can be to lower the activity level, move indoors or move to another location.

Hence, in a first aspect the invention provides a method for determining a transportation direction for a user, the method comprising: (a) receiving a current location of the user; (b) receiving a pollution based input value related to air pollution in a geographical area including the current location; and (c) determining the transportation direction using the pollution based input value such that the user is subjected to a lowest level of pollution and/or such that a predefined maximum level of pollution to which the user is subjected is not exceeded.

With such method it is possible to guide person via a safe(r) route to a destination and/or help a person avoid areas with relative high pollution. Further, such method may also allow adapting the direction in relation to the activity of the person. For instance, when activity is higher (e.g. when the person is running) a trade-off between exposure to pollution and length of a route may be different than when activity is lower (e.g. when the person is walking). Further, such method also allows people who are riding (e.g. a bike) or walking, or otherwise moving for leisure purposes or recreation, choose directions with relatively less pollution.

Herein, the term pollution may refer to the molecules or particles in air which in high(er) concentrations are considered unhealthy. Especially, it relates to air in the troposphere, such as in about a few kilometers, or even a few hundred meters over the earth surface. The molecules or particles which may especially of interest are ozone, nitrogen oxides ($NO_x$, especially $NO_2$), sulfur dioxides ($SO_x$, especially $SO_2$), ammonia ($NH_3$), particulates (particulate matter, like originating from volcanoes, dust storms, forest and grassland fires, living vegetation, and sea spray, or originating from human activities, such as the burning of fossil fuels in vehicles, power plants and various industrial processes), etcetera. Hence, the present invention may take into account smog situation, ozone generation due to traffic, pollen, etc.

As indicated above, the invention provides a method for determining a transportation direction for a user.

The user is not part of the claimed method, but the method is especially designed for being used by a user. The user is especially a human (e.g. adult or child) who is walking or intends to walk, who is riding or intends to ride (a horse, a bicycle, any un-motorized wheeled vehicle), is running or intends to run, or anyhow is moving or intends to move in a un-motorized way. However, the user may also be a human in a motorized wheel chair or intending to use such motorized wheel chair. However, the user may also be a human using (or intending to use) a motorized transport means designed for propagation on a road, such as a motorized cycle, a motor, a car, a truck, a van, a coach, etc. etcetera. Even, the user may be a human using (or intending to use) a transport means for waterways, like a sailboat, etc.

Herein, the term "transportation direction" is used. This may amongst others imply that on a display and/or with sound, or optionally alternatively or additionally with other means, the user may be indicated in which direction the user should move. For instance, this may imply choosing another side of the road, choosing a parallel road, choosing another road, etc. In this way, the exposure to pollution may be reduced. The term "transportation" especially indicates a movement. Hence, instead of "transportation direction" also the term "movement direction" might be used. The term "transportation direction" does not necessarily imply the use of a transportation means. As indicated above, the method may also be used for a user who is e.g. walking or running.

The bases of the transportation direction may include the current position ("current location") and optionally a target position ("destination location"). Hence, the method in general may at least comprise receiving a current location of the user. The current location may be provided by manually entering data about the current location. However, in general a device, such as a wearable (e.g. a GPS-enabled wearable), will be used that is able to determine its location.

Hence, in embodiments the method further comprises determining an average historical transportation direction based on a time frame preceding the current location, wherein the method comprises determining the transportation direction in average being in line with the average historical transportation direction. For instance, a user having a walk or a jogger running along a street from a starting (like home) point also being the destination point (home) may choose its own route via a fixed route or via a spontaneous chosen route. Here, the method may be used to indicate a direction to areas where exposure to pollution is less or minimal. This might even, e.g. imply walking at the other side of a road, or choosing a parallel road, for instance in view of the traffic and wind direction (see also below). Hence, the term "transportation direction" may in embodiments also refer to a plurality of transportation directions, which may optionally also be indicated with an indication related to the pollution.

For instance, a wearable may, e.g. schematically, show a 360° indicator with colors or hues indicating desirable and less desirable directions. For instance, green may indicate a direction where exposure to pollution is lower than red. By viewing the screen of the wearable, the user may choose, even while walking or running, a direction where pollution may be less than in other directions.

The term "average historical transportation direction" may e.g. refer to the average transportation direction over a predetermined time period, such as 30 seconds, or 60 seconds, or 120 seconds. Hence, in embodiments instead of the term "average historical transportation direction" also the term "effective direction over a certain time period" may be chosen. The predetermined period may in embodiments be selected from the range of 6 seconds to 60 minutes, like 30 seconds to 15 minutes. Optionally, such time period may only start after a last change in direction. The method may include determining the predetermined period and/or other parameters to determine the average historical transportation direction. For instance, the average historical transportation direction may be the direction followed after a change in direction. In embodiments, parameters may be set for the condition(s) for a change in direction.

In other embodiments, the destination location may be used as input value for determining the transportation direction. This may especially be the case when a user desires to move to another place than a starting location, such as from home to work (or vice versa), or from home to a shopping mall, or from work to a customer, etc. Hence, in embodiments the method may further comprise defining a destination location, and determining the transportation direction from the current location to the destination location (DL) using the pollution based input value such that the user is subjected to a lowest level of pollution and/or such that a predefined maximum level of pollution to which the user is subjected is not exceeded.

For instance, a wearable may (schematically) provide one or more alternative choices for reaching the destination, wherein with colors or hues, etc., desirable and less desirable routes (and thus directions) may be indicated. For instance, green may indicate a direction where exposure to pollution is lower than red. By viewing the screen of the wearable, the user may choose, even while walking or running, a direction where pollution may be less than in other directions, for reaching the destination location. Of course, instead of colors or hues, or in addition thereto, values may be provided for indicating the pollution. Additionally or alternatively, text may be provided for indicating the pollution, such as "high", "low", "safe", etcetera.

The method may also allow in embodiments input of the relevant pollution to be evaluated. For instance, in embodiments, as input, the user may choose between one or more of ozone, nitrogen oxides, sulfur dioxides, ammonia, particulates, etcetera. Alternatively or additionally, the user may choose between different particulates to be evaluated. For instance, the user may choose "smog", or the user may use "pollen", etcetera. In embodiments, the user may choose UFP and/or FP.

As indicated above, the method may further comprise receiving a pollution based input value related to air pollution in a geographical area including the current location. This pollution based input value will in general be retrieved from servers where actual information on pollution is available or wherein information is available from which actual information on pollution can be retrieved.

For instance, there may be a nation-wide sensing system for sensing one or more of ozone, nitrogen oxides, sulfur dioxides, ammonia, particulates (like e.g. one or more of UFP and FP), etcetera. This may include one or more of local sensors on the ground, mobile sensors in the air (like balloons, drones, etc.), and sensors in orbits around the earth, such as satellites. Therefore, in embodiments the pollution based input value is based on real-time pollution information in the geographical area from a pollution information server.

The term "pollution based input value" may refer to a value, or a plurality of values, especially a plurality of values related to roads or geographical coordinates. Hence, the term "pollution based input value" may also refer to a plurality of values, including geographical representations, such as maps, with pollution based input value. The "pollution based input value" may refer to a value that indicates the (local) concentration of one or more of ozone, nitrogen oxides, sulfur dioxides, ammonia, particulates, etcetera. Hence, such value may be a pollution value. However, such values may also be processed, for instance into categories, into averages in time, such values may be corrected, etc. Hence, such values that may be measured and may be used directly or may be used after processing are herein indicated as "pollution based value". In embodiments, the data may be available (on a server) as processed data. The term "input" in "pollution based input value" refers to the fact that the pollution based value is also used as input value for determining the transportation direction.

The term "pollution information server" (see further also below) may refer to any server that may host information concerning pollution or information from which pollution data may be derived, which are both indicated as pollution based value. Hence, in embodiments the method includes retrieving pollution based value and using these pollution based value as pollution based input value.

Based on the input, i.e. the current location and the pollution based input value, the method determines the transportation direction such that the user is subjected to a lowest level of pollution and/or such that a predefined maximum level of pollution to which the user is subjected is not exceeded. In embodiments, the user may indicate or the method may be configured to always choose directions wherein the user will be subjected to a lowest level of pollution. However, in other embodiments, the user may indicate or the method may be configured to choose or to allow a choice wherein time, type or roads, or other (additional) user input data are balanced against the level of pollution. Nevertheless, it may still be possible that the method allows or is configured to have a constraint in that a predefined maximum level is defined. Such predefined maximum level may be defined in e.g. the standard settings of a device or a user may choose such predefined maximum level.

The pollution based input value(s) are preferably relatively up to date, or even real time. Of course, one could use a monthly, quarterly, yearly, or even longer average, but especially, the pollution based input value are essentially real-time. This may for instance be achieved by not (only) basing the pollution based input value on measured emission data, but by (also) using other data from which the pollution based input value can thus be derived. This does not imply that both essentially real time data and less actual data are used, or that in addition to essentially real time data also e.g. forecast data may be used. As indicated below, e.g. weather data may also be used, but one could e.g. also, in addition to e.g. particulate emission from traffic (see also below), take into account wind driven pollution from (adjacent) industry.

A good approximation, especially for essentially real-time data, is using (real time) traffic data, as traffic may have a substantial impact on the local generation of particulate matter, nitrogen oxides, sulfur oxides, etcetera. Hence, in embodiments the method may further comprise deriving the pollution based input value from traffic data related to motorized transport vehicles in the geographical area.

Such traffic data may be e.g. derived from camera's along roads, by satellite monitoring, but also by servers that communicate with mobile devices such as route navigation devices (GPS navigation) and/or smart phones. Therefore, in embodiments the method may comprise retrieving the traffic data from one or more of a traffic information server, a telecommunication server for mobile communication devices, and a navigation server. The traffic information server may be a server where information is available about traffic, such as e.g. based on cameras along the roads. Of course, the traffic information server may also use other sources of information, such as telecommunication information and/or navigation information. A telecommunication server may especially be used for the data that can be derived from smartphones. Such phones can be tracked or the communication with communication points can be tracked, on the basis of which traffic can be evaluated. The latter may also apply to a navigation server, where the navigation device can be tracked or the communication with communication points (including satellites) can be tracked, on the basis of which traffic can be evaluated.

Hence, it is not excluded that a single server may provide different types of data. Further, it is also not excluded that a plurality of servers may be used to provide the pollution based input value(s), such as e.g. traffic data.

When using traffic data as basis for the pollution based input value it may not always be clear whether the traffic is really (locally) polluting or not. For instance, a distinction between fossil fuel based motorized vehicles and electrical energy based motorized vehicles may not (easily) be derivable from telecommunication data. Therefore, it is desirable, especially in view of the increasing number of electrical cars, to distinguish between polluting vehicles and non-polluting vehicles, or even between e.g. relatively highly polluting vehicles and relatively low polluting vehicles. Therefore, in embodiments (of the method) the traffic data may comprise pollution generating vehicle data and non-pollution generating vehicle data; especially in such embodiments the pollution based input value may be derived from the pollution generating vehicle data. In this way, it may be distinguished between those vehicles that generate pollution, and those that do not. Only the relevant data may have to be used in the method.

In embodiments, vehicles may be equipped with transmitters, such as navigation devices, that may also be configured to provide information about the emission of the individual motorized transport vehicle. This may e.g. be a simple distinction between electrical and non-electrical, but may optionally also be smarter, such as the (average) amount of pollution, such as particulate emission or $CO_2$ emission, etcetera. Therefore, in embodiments, (a) the pollution based input value may be based on information on individual motorized transport vehicles including information about their emission from a server, and/or (b) wherein the pollution based input value may be based on information from a server that is permanently or temporary in communication with transmitters comprised by individual motorized transport vehicles, which transmitters are configured to provide information about the emission of the individual motorized transport vehicle.

In embodiments, the pollution based input value may also be based on speed dependent pollution based input value. The pollution of a car depends on speed and acceleration. Hence, in embodiments when the type of car is known and its speed an even better approximation of the emissions may be possible. Alternatively or additionally, an average speed of traffic may be used as (further) basis of the pollution based input value.

Therefore, in embodiments (of the method) the traffic data may comprise pollution generating vehicle data based on individual motorized vehicles. The pollution based input value may thus be based on individual motorized vehicles. As indicated herein "based on" may also imply that the pollution data of individual motorized vehicle are processed, such as into the addition of the pollution data over a specific time in a specific area (at a specific time).

Especially, the method may in embodiments further comprise permanently or regularly updating the pollution based input value and consequently updating the transportation direction thereon. For instance, each second or each 10 seconds or each 30 seconds, or each minute, or each 5 minutes, or each 10 minutes, etc., the pollution based input value may be refreshed or checked on a change. Hence, there can be a permanent or regular contact with a server having pollution based input value available.

The method may not only allow indicating a transport direction. In embodiments, the outcome may also be an advice to get indoors instead of (indicating) a transportation direction or in addition to (indicating) a transportation direction (where the user is subjected to a lowest level of pollution and/or such that a predefined maximum level of pollution to which the user is subjected is not exceeded). In embodiments, the method may further include an advice concerning the method of transportation. For instance, walking or riding with a bike the route may sometimes be shorter in time (than riding with a car) but this may have to be balanced against the exposure to pollution (over the travelling time)(wherein in the exposure also the physical activity may be taken into account). Hence, in embodiments the input information may further comprise options of transport information wherein in embodiments the options of transport information may at least comprise one or more selected from the group consisting of motorized transport and non-motorized transport. In yet further embodiments, the method may further include an advice concerning one or more of (i) slowing down activity and (ii) wearing a mask, e.g. an air filtering mask, or a mouth cap.

Further, the weather, such as the wind speed and wind direction, may also have an impact on the transportation direction. For instance, in case of some non-motorized ways of transport, like walking or running, it may be an option to travel at both sides of a road. This may lead to substantially different exposures of pollution. Therefore, in embodiments the method may further comprise retrieving weather input information in relation to the geographical area; and, even more especially (also) updating the transportation direction using the weather input information. Such weather input information may be retrieved from a weather server.

The method may also allow taking into account the activity or activity level of a user. For instance, when a user is highly active, especially a user that may have to take into account his or her health e.g. in view of respiratory issues, it may be desirable to especially take into account exposure to pollution. Therefore, in embodiments the method may further comprise retrieving a human activity based input value, wherein the human activity based input value is based on activity data from a portable device configured to sense an activity level of the human wearing the portable device; and, even more especially (also) updating the transportation direction using the human activity based input value. In embodiments, (a) the portable device may comprise a device configured to sense one or more of steps and motion of the human, and/or (b) the portable device may comprise a device configured to sense one or more of blood pressure, heart beat, respiratory sound, and perspiration of the human. Especially, the portable device is configured to derive activity data from the sensed data. Therefore, in specific embodiments the method may include generating said transportation direction in dependence of (also) one or more of (i) a predefined maximum activity level and (ii) a predetermined maximum exposure to the pollution.

By taking into account the activity level of the user, situations or circumstances detrimental to the health of a user can be avoided. For example, when the breathing rate of a user is high, the intake of polluted air is higher compared to a low breathing rate of the user. Thus, the transportation direction may be selected in dependence on a breathing rate (=activity level) of the user and the exposure to pollutants related to that breathing rate. Such a breathing rate (=activity level) and/or predetermined maximum exposure to pollutants may be set by the user or wirelessly set via a server. Breathing rate (=activity level) linked to maximum exposure to pollutants may differ between different persons, depending on the health condition of the user. For example, a person with a respiratory condition should be exposed to less polluted air than a healthy person to avoid a respiratory attack. Therefore, the values with respect to activity level and linked maximum pollutant exposure may be configurable.

According to an embodiment, the predefined maximum level of pollution used to determine the transportation direction is linked to the activity or activity level of a user represented by the human activity based input value.

In yet a further aspect, the invention also provides a data carrier having stored thereon program instructions, which when executed by a processing apparatus, causes the processing apparatus optionally by operating together with one or more other processing apparatus, to execute the method as defined herein. Instead of the term "data carrier" also the terms "record carrier" etc. may be used. The record carrier, such as a USB stick, a CD, DVD, etc.) may store a computer program for executing the herein described method, optionally together wine one or more other processing apparatus. Hence, the computer program product, when running on a computer or loaded into a computer, brings about, or is capable of bringing about, the method as described herein. The computer-readable medium and/or memory may be any recordable medium (e.g., RAM, ROM, removable memory, CD-ROM, hard drives, DVD, floppy disks or memory cards) or may be a transmission medium (e.g., a network comprising fiber-optics, the world-wide web, cables, and/or a wireless channel using, for example, time-division multiple access, code-division multiple access, or other wireless communication systems). Any medium known or developed that can store information suitable for use with a computer system may be used as the computer-readable medium and/or memory.

The processing apparatus especially comprises a controller or processor, and may further comprise a memory. The controller/processor and the memory may be any type. The processor may be capable of performing the various described operations and executing instructions stored in the memory. The processor may be an application-specific or general-use integrated circuit(s). Further, the processor may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit.

Each of the above systems may be utilized in conjunction with further systems. As indicated above, the processing apparatus may execute the method as defined herein, optionally by operating together with one or more other processing apparatus. For instance, part of the processing of the input data into the transportation direction may be done locally with a device such as a navigation device (GPS navigation device) and part may be done in the cloud. For instance, maps may be stored locally or may be stored in the cloud, etcetera.

In yet a further aspect, the invention also provides a computer implemented system for providing a transportation direction to a user, the computer implemented system comprising an information device for informing a user about the transportation direction (and optionally other options, such as staying home, slowing down activity, etc., see also above), a communication system for communication with a remote server for retrieving a pollution based input value related to air pollution in a geographical area including the current location, a processing apparatus, and a storage device with program instructions stored thereon for having the processing apparatus, and optionally by operating together with one or more other processing apparatus, to execute the method as defined herein.

As indicated above, the system may also be used for navigation purposes wherein a destination location can be indicated (via a user interface). Hence, the system may in embodiments further comprise a user interface for at least inputting of an input destination value which defines a destination location.

Therefore, in an aspect the invention also provides a computer implemented system for providing a transportation direction to a user, the computer system comprising an information device for informing a user about the transportation direction, a communication system for communication with a remote server for retrieving a pollution based input value related to air pollution in a geographical area including the current location (and the destination location), a processing apparatus, and a storage device with program instructions stored thereon for having the processing apparatus and optionally by operating together with one or more other processing apparatus, to execute the method as defined herein.

As indicated above, the phrase "pollution based input value related to air pollution" may especially indicate pollution based input value related to estimated and/or measured air pollution.

BRIEF DESCRIPTION OF THE DRAWINGS

Embodiments of the invention will now be described, by way of example only, with reference to the accompanying schematic drawings in which corresponding reference symbols indicate corresponding parts, and in which.

The schematic drawings are not necessarily on scale.

DETAILED DESCRIPTION OF THE EMBODIMENTS

Currently, people have no easy way to find out how polluted their immediate surrounding is and what to do about it. Devices that can measure such pollution are heavy, cumbersome and expensive. In addition almost nobody can quantify the consequences of activity. On the internet data are available, but that data may not be accurate enough, and it may be cumbersome to get these data.

Amongst others, this invention can give a personalized advice on how to react and what to do (depending on the exact configuration). An element may be a clever piece of software running on a mobile phone or a health watch, etcetera. The device may further comprise an accelerometer to monitor the activity of the user, a GPS to monitor the location of the user and to assist in determining the activity level, and an internet connection, e.g. to download data from which the local FP and UFP is calculated. This can easily be extended to include other pollutants such as $NO_x$, ozone etc.

National governments have setup a grid of measurement stations on many locations. There are websites that collect these data worldwide. From the data a localized detailed map can be calculated by using model calculations. Such maps are detailed enough to provide air pollution from individual highways. As indicated above, the deposited amount of pollutant can be calculated from the activity of the person by using the additional air breathed in plus the activity dependent deposition fraction. An advice can now be given when: calculated pollution*enhanced deposition fraction*(1+fraction additional air)>threshold level. The threshold level can be for instance the 24 h average norms. The advice can be to lower the activity (because then the additional air and the enhanced deposition fraction become lower) or to move to an area with lower air pollution. The latter can be as simple as to move to the other side of a street in order to get upwind from the motorized traffic.

As a refinement, local (real time) traffic information can be included. The main reason is that traffic causes local spikes in the air pollution level. This information is available at for instance car navigation producers. Such data may be used to determine the actual local traffic intensity. Using the maps from the model calculations, the traffic data, the wind direction and the position of the person, an accurate estimate of the relevant pollution can be made.

Figure 1:
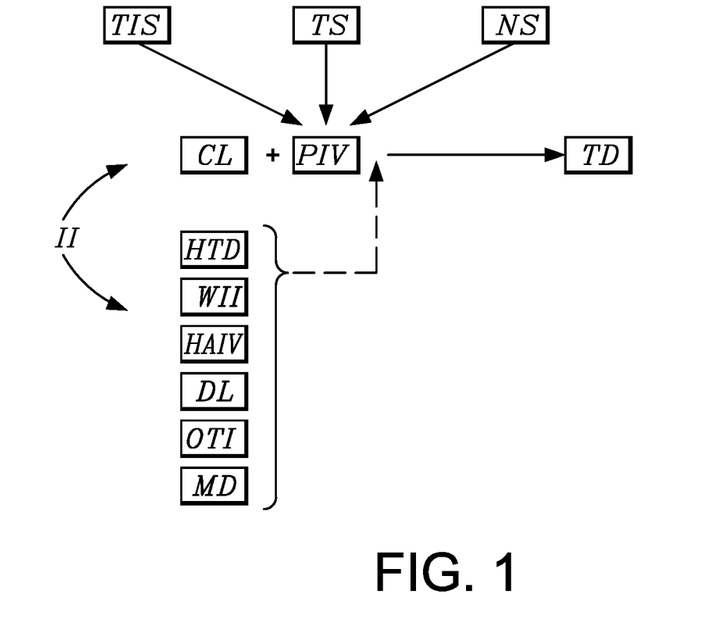
FIG. 1 schematically depicts some aspects of embodiments of the method.

FIG. 1 schematically depicts an embodiment, in the form of a flow chart, of the method for determining a transportation direction TD for a user. The user is not depicted. As input information II a current location CL of the user and a pollution based input value PIV related to air pollution in a geographical area including the current location CL are used. On the basis thereof, the transportation direction TD can be determined, such that the user is subjected to a lowest level of pollution and/or such that a predefined maximum level of pollution to which the user is subjected is not exceeded.

The pollution based input value PIV can e.g. be derived from e.g. traffic data from one or more of a traffic information server TIS, a telecommunication server TS for mobile communication devices, and a navigation server NS.

Further optional input information may e.g. be an average historical transportation direction HTD. In this way, the method may determine the transportation direction TD in average being in line with the average historical transportation direction HTD.

Also weather input information WII in relation to the geographical area may be retrieved, for adapting and updating the transportation direction TD using the weather input information WII.

Also a human activity based input value (HAIV) may be used as input, which value may reflect the activity or intensity of physical activity. Such value may be retrieved from a portable device (see also FIG. 2b) configured to sense an activity level of the human wearing the portable device. This information may be used for adapting and updating the transportation direction TD using the human activity based input value HAIV.

A user may also indicate the desired destination location DL. This may allow determining the transportation direction TD from the current location CL to the destination location DL using the pollution based input value (such that the user is subjected to a lowest level of pollution and/or such that a predefined maximum level of pollution to which the user is subjected is not exceeded).

In embodiments, e.g. also options of transport information OTI may be offered to the user, or the method may e.g. include providing such options as alternatives for different directions. The options of transport information OTI may at least comprise information from motorized transport and/or non-motorized transport.

Reference MD indicates the mode of transport. For instance, a user may indicate the desire to walk, or to ride a bicycle, or to use a car, or to use public transport, etc. etcetera.

Figure 2A:
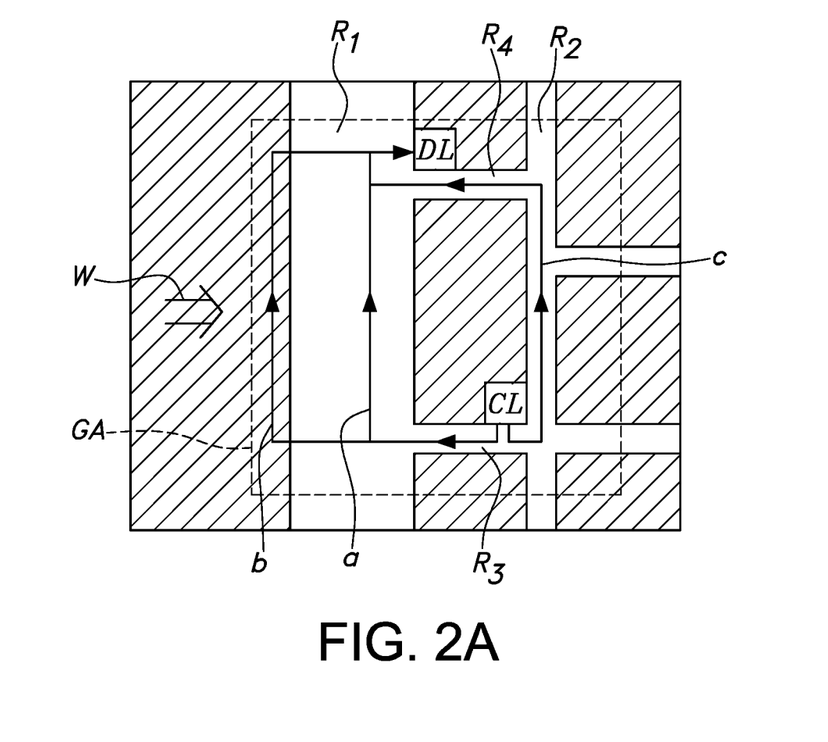
FIG. 2a-2c schematically depicts a map with geographical area and possible routes.

FIG. 2a very schematically depicts a map with a main road R1, a parallel smaller road R2 and connecting roads R3 and R4. Reference W indicates the wind direction. Several options to travel from the current location CL to the destination location DL can be chosen, indicated with references a, (R3, R1, via the road R1, such as by car or bicycle), b (R3, R1, aside from the road at the left side, e.g. walking), and c (R3, R2, via the road R2, such as by car or bicycle), R4, R1). Dependent upon the input parameters, such as the wind, the traffic on the roads R1-R4, and the desire to travel safe or fast, etc., the method may provide the direction when traveling from the current location to the destination location.

Note that the current location changes in time, and thus the method may also update the transportation direction, amongst others also in dependence of changes in the pollution.

Figure 2B:
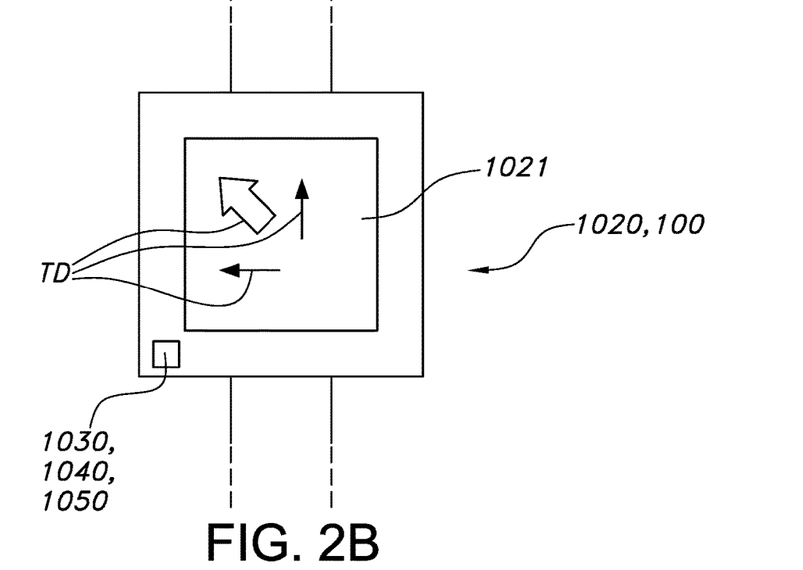
Figure 2C:
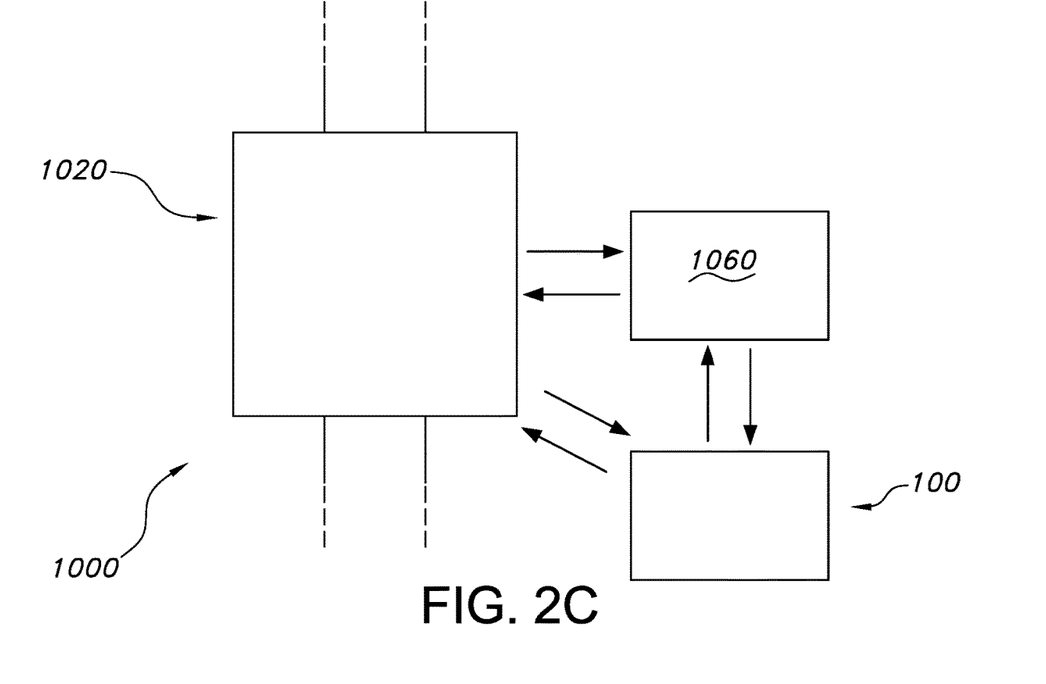

FIGS. 2b-2c schematically depict parts of a computer implemented system 1000 for providing a transportation direction TD to a user. The computer implemented system 1000 comprises an information device 1020, such as a wearable (especially comprising GPS), like a health watch, etcetera., for informing a user about the transportation direction TD.

Further, the computer implemented system 1000, especially the information device 1020, may comprise a communication system 1030 for communication with a remote server for retrieving a pollution based input value PIV related to air pollution in a geographical area including the current location, a processing apparatus 1040, and a storage device 1050 with program instructions stored thereon for having the processing apparatus 1040 and optionally by operating together with one or more other processing apparatus, for executing the method as described herein. Reference 1021 indicates a display, for indicating the transportation direction. Different ways of indicating, such as here schematically indicated with the thicknesses of the arrows, may indicate the safety. The information device may include a user interface, such as a graphical user interface integrated with the display 1021. FIG. 2c very schematically depicts the device 1020 optionally communicating with another processing apparatus 1060 and/or optionally communicating with a portable device 100 that can measure the activity of the user, for determining the transportation direction. Such portable device may be integrated in the information device 1020. The other processing apparatus may be a server or a processing apparatus communicating with a server.

The term "substantially" herein, such as in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A method for determining a transportation direction for a user, the method comprising:
  receiving a current location of the user;
  receiving a pollution based input value related to air pollution in a geographical area including the current location; and
  determining the transportation direction using the pollution based input value such that the user is subjected to a lowest level of pollution and/or such that a predefined maximum level of pollution to which the user is subjected is not exceeded;
  characterized in that, the method further comprises:
  retrieving a human activity based input value, wherein the human activity based input value is based on activity data from a portable device configured to sense an activity level of the human wearing the portable device; and updating the transportation direction using the human activity based input value.

2. The method according to claim 1, comprising deriving the pollution based input value from traffic data related to motorized transport vehicles in the geographical area.

3. The method according to claim 1, the method further comprising determining an average historical transportation direction based on a time frame preceding the current location, wherein the method comprises determining the transportation direction in average being in line with the average historical transportation direction.

4. The method according to claim 1, comprising retrieving the traffic data from one or more of a traffic information server, a telecommunication server for mobile communication devices, and a navigation server.

5. The method according to claim 1, wherein the traffic data comprises pollution generating vehicle data and non-pollution generating vehicle data; and wherein the pollution based input value is derived from the pollution generating vehicle data.

6. The method according to claim 1, wherein (a) the pollution based input value is based on information on individual motorized transport vehicles including information about their emission from a server, and/or (b) wherein the pollution based input value is based on information from a server that is permanently or temporary in communication with transmitters comprised by individual motorized transport vehicles, which transmitters are configured to provide information about the emission of the individual motorized transport vehicle.

7. The method according to claim 1, wherein the pollution based input value is based on real-time pollution information in the geographical area from a pollution information server.

8. The method according to claim 1, further comprising:

retrieving weather input information in relation to the geographical area; and updating the transportation direction using the weather input information.

9. The method according to claim 1, wherein (a) the portable device comprises a device configured to sense one or more of steps and motion of the human, and/or wherein (b) the portable device comprises a device configured to sense one or more of blood pressure, heart beat, respiratory sound, and perspiration of the human; and wherein the portable device is configured to derive activity data from the sensed data.

10. The method according to claim 1, wherein the method includes generating said transportation direction in dependence of one or more of (i) a predefined maximum activity level and (ii) a predetermined maximum exposure to the pollution.

11. The method according to claim 1, further comprising defining a destination location, and determining the transportation direction from the current location to the destination location using the pollution based input value such that the user is subjected to a lowest level of pollution and/or such that a predefined maximum level of pollution to which the user is subjected is not exceeded.

12. The method according to claim 1, further comprising permanently or regularly updating the pollution based input value and consequently updating the transportation direction thereon.

13. A data carrier having stored thereon program instructions, which when executed by a processing apparatus, causes the processing apparatus optionally by operating together with one or more other processing apparatus, to execute the method according to claim 1.

14. A computer implemented system for providing a transportation direction to a user, the computer implemented system comprising an information device for informing a user about the transportation direction, a communication system for communication with a remote server for retrieving a pollution based input value related air pollution in a geographical area including the current location, a processing apparatus, and a storage device with program instructions stored thereon for having the processing apparatus and optionally by operating together with one or more other processing apparatus, to execute the method according to claim 1.

* * * * *